United States Patent
Pond et al.

(10) Patent No.: US 7,490,837 B2
(45) Date of Patent: Feb. 17, 2009

(54) EQUIPMENT CADDIE SYSTEM

(75) Inventors: Gary J. Pond, Racine, WI (US); Scott N Schmidt, Bonduel, WI (US)

(73) Assignee: Inter-Med, Inc., Racine, WI (US)

( * ) Notice: Subject to any disclaimer, the term of this patent is extended or adjusted under 35 U.S.C. 154(b) by 329 days.

(21) Appl. No.: 11/255,364

(22) Filed: Oct. 21, 2005

(65) Prior Publication Data

US 2007/0093118 A1    Apr. 26, 2007

(51) Int. Cl.
A61C 13/38 (2006.01)
A61G 15/00 (2006.01)
B62B 3/00 (2006.01)

(52) U.S. Cl. .................. 280/47.35; 433/77; 433/79
(58) Field of Classification Search ............... 433/98, 433/77, 79, 27; 248/129, 405, 669; 280/47.35, 280/47.41, 47.34
See application file for complete search history.

(56) References Cited

U.S. PATENT DOCUMENTS

| | | | | |
|---|---|---|---|---|
| 2,351,943 | A | * | 6/1944 | Ebbers et al. ................. 433/77 |
| 3,210,846 | A | * | 10/1965 | Balkin ......................... 433/98 |
| 3,949,480 | A | * | 4/1976 | Page ........................... 433/27 |
| 4,160,323 | A | | 7/1979 | Tracy |
| 4,715,573 | A | * | 12/1987 | Liegel ........................ 248/129 |
| 4,826,432 | A | * | 5/1989 | Roseiro ....................... 433/79 |
| 4,842,233 | A | * | 6/1989 | Rusin ......................... 248/405 |
| 4,941,873 | A | | 7/1990 | Fischer |
| 4,958,963 | A | * | 9/1990 | Perrault ...................... 433/77 |
| 5,013,240 | A | | 5/1991 | Bailey et al. |
| 5,112,019 | A | | 5/1992 | Metzler et al. |
| 5,211,558 | A | | 5/1993 | Bailey et al. |
| 5,250,027 | A | | 10/1993 | Lewis et al. |
| 5,536,084 | A | | 7/1996 | Curtis et al. |
| 5,647,491 | A | | 7/1997 | Foster et al. |
| 5,655,905 | A | | 8/1997 | Jaimes et al. |
| 5,997,297 | A | | 12/1999 | Coburn et al. |
| 6,022,088 | A | | 2/2000 | Metzler |
| 6,626,445 | B2 | | 9/2003 | Murphy et al. |

OTHER PUBLICATIONS

MTC Multi-Task Carts, Obtura Spartan.
Ergonomic Products: Dental Office Equipment for Performance & Productivity.

* cited by examiner

Primary Examiner—Hau V Phan
(74) Attorney, Agent, or Firm—Ryan Kromholz & Manion S.C.

(57) ABSTRACT

A portable medical apparatus for holding a plurality of surgical tools wherein at least one of said tools is electrically powered and includes a power supply cord and a power plug is disclosed. The apparatus comprises a housing having at least one electrical outlet for removably receiving the power plug is disposed within said inner shell. The housing includes an upstanding wall having at least one area for receiving and supporting a power supply cord. A removable enclosure lid is received by the housing. An upright member supports the housing and provides a passageway for a conductor in electrical communication with the electrical outlet. A base supports the upright member and includes a laterally extending leg having a channel for receiving the electrical conductor. The leg is apertured to receive a connector for attachment to the electrical conductor.

12 Claims, 13 Drawing Sheets

EQUIPMENT CADDIE SYSTEM

BACKGROUND OF THE INVENTION

The present invention relates to transportation devices for medical and dental equipment and, more specifically, caddies and similar portable equipment for transporting, powering and controlling, and storing medical and dental equipment.

Several different tools may be utilized for any single surgical procedure. Since different tools may be used in different combinations for different procedures, it is advantageous to store several tools, such as high and low speed drills, suction and rinsing devices, ultrasonic scalers, light-emitting devices, and other devices, in a centralized place. Likewise, these devices should be arranged in close proximity to pumps, compressors, reservoirs, electrical supplies and the like that are required for operating the individual tools. Normally, each tool or attachment had individual attachments that would attach the tool to the source power or fluid supply located in a permanent place of a room or building. Since tools are utilized for different procedures that may take place at different locations or rooms within a dental office, it is advantageous that not only the tools may be movable from one area to another, but also the base structure to which they are connected is also movable. Thus, it is beneficial to provide a transportable caddie system for transporting the necessary equipment and tools from one station to another.

The prior art has developed portable workstations. Bailey et al., U.S. Pat. No. 5,211,558, and Tracy, U.S. Pat. No. 4,160,323, provide examples of portable dental cabinets and workstations. However, current workstations tend to be more cumbersome and bulky than necessary. The workstations generally do not allow easy access to connections and adaptors for specific tools, especially when those tools need to be serviced or replaced. In many instances, when an individual tool needs servicing, the entire workstation must be sent away for servicing. Furthermore, accessories, such as fluid reservoirs and control panel consoles, are usually situated within a storage or housing assembly, which makes access for these accessories difficult, especially if service or maintenance is required. Likewise, it is also desirable to have more compact workstations than currently used in the prior art. To address these issues, a compact, easily serviceable, portable workstation is contemplated.

On the other end of the medical spectrum lay devices such as IV poles and poles for transporting peristaltic pumps. These devices are generally narrow poles that may be easily transportable from one area to another. However, these devices generally are not designed for tools or accessories to be added onto the poles. If extra accessories are added to the poles, they become awkward to transport, similar to the equipment caddies discussed above, and also lack the necessary stability for transporting such accessories.

Though compact workstations and equipment caddies have been developed, most are generally more cumbersome than desired. Moving a workstation from one room to another may be an arduous task. Even moving from one side of a patient to the other, for instance to allow the workstation to be used easily by left and right handed people, may not be easily accomplished. Currently existing caddies are movable from one room to another between procedures, but generally not adequately mobile during a procedure. Accordingly, there is a need for an easily movable, compact equipment caddie that will adequately provide the necessary tools and accessories a medical practitioner may need for a specific medical procedure. Likewise, the equipment caddie must have the ability to power several different attachments in an efficient and organized manner.

SUMMARY OF THE INVENTION

The present invention provides a compact, organized transport for medical accessories and tools. The transport or equipment caddie comprises three general sections: a housing, a support section, and a base. The housing has electrical outlets disposed within the bottom section of the housing that will allow various tools to be connected to the equipment caddie. The housing further has an upstanding wall with specific areas for receiving and supporting electrical cords attached to the tools and accessories used in conjunction with the equipment transport. The arrangement prevents cords from different tools to become tangled and further allows the cords to be easily accessible, if necessary.

The support section supports the housing. The support section is preferably an upstanding, hollow post located centrally of the housing. The post contains an electrical conductor that is connected to the electrical outlets within the housing. The support may also support other external accessories, such as control panels, fluid reservoirs, storage containers, and handpiece mounting devices such as cross bars and other handpiece mounting functions.

The base supports the support section, and is attached to wheels or other means that provides movement for the base and the equipment caddie. The base may have laterally extending legs that include channels for receiving at least one conduit and having apertures to receive connectors for attachment to a power supply, allowing power to be supplied through the caddie to the dental tools and various controls or apparatuses that require power. Additionally, the base will have apertures to receive foot pedals and other controls being directly wired or plumbed, removable via mating connectors, or having wireless function and capability, all having single level and variable level switching and controlling with multiple switching ability.

A fluid conduit or conduits may also pass from a fluid port located in the base through the base and the support member, terminating at various and multiple fluid outlets located in the housing, where it may be used for any of the various attached accessories and tools.

Fluid conduits such as air/pneumatic conduit may also pass from an air/pneumatic port located in the base through the base and the support member, terminating at various and multiple air/pneumatic outlets located in the housing, where it may be used for any of the various attached accessories and tools.

The caddie may have electrical connectors, fluid ports, and air/pneumatic ports located on other sections of the caddie. Also, the caddie may have a cable manager that will assist in preventing individual dental tool cords, lines, conduit, and tubing from becoming tangled.

Possible attached dental tools include, but are not limited to:
  Ultrasonic scalers
  Air/water syringes
  High speed/low speed rotary devices
  Rotary devices and drills
  Suction devices
  Light and curing sources
  Aspirators
  Irrigation devices
  Gutta Percha systems
  Apex Locators The advantages of the present invention will be more clearly understood from the following detailed description and drawings.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structure. While the preferred embodiment has been described, the details may be changed without departing from the invention, which is defined by the claims.

As referred throughout the description, fluids include both liquids and gases. It is understood that reference to elements for use with a fluid or fluids or air/fluids generally includes any gases or liquids and should not be limited to either. Unless specified that an element or device is only used in conjunction with a specific fluid or gas, the element should not be limited in scope.

Figure 1:
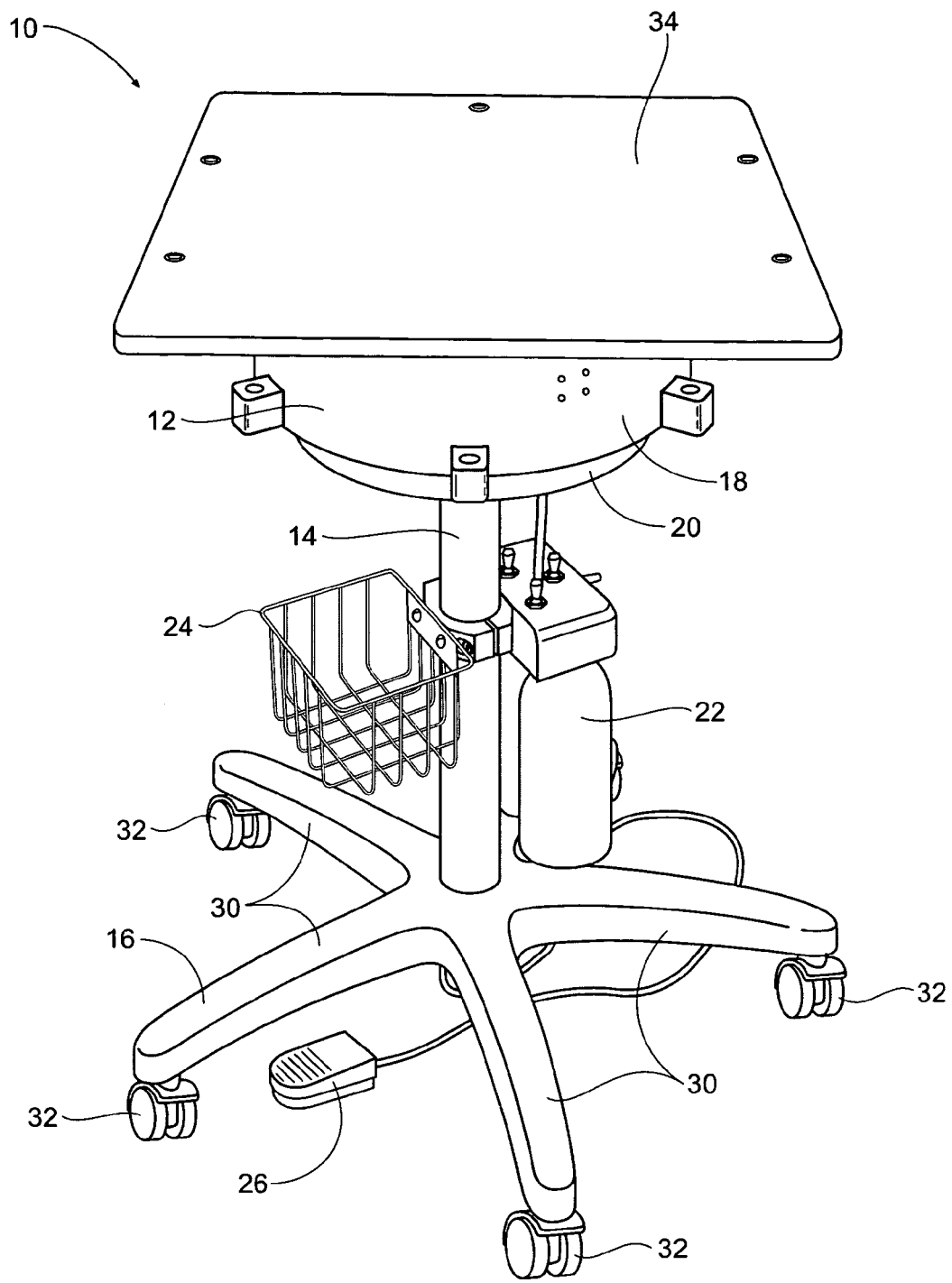
FIG. 1 is a perspective view of an equipment caddie in accordance with the present invention.

FIG. 1 shows a perspective view of a portable medical apparatus or equipment caddie 10 designed in accordance with the present invention. The apparatus 10 generally comprised of three sections: a housing 12, an upright member 14, and a base 16. The housing 12 is comprised of an outer shell 18 and an inner shell 20 that is in a spatial relationship with the outer shell 18. The shells 18 and 20 preferably have a cylindrical shape, which adds a safety feature to the apparatus 10 when the apparatus is being moved or transported, since there are no sharp edges or points on the housing 12 of the apparatus 10.

Still referring to FIG. 1, the upright member 14 has a plurality of accessories extending laterally outward from the support 14. For example, and with no intent to limit possible accessories that may be attached to the upright member 14, a fluid reservoir 22 and a storage bin 24 are shown attached to the support 14. A foot pedal or control 26 may also be attached to the apparatus 10.

As further shown in FIG. 1, the upright member 14 is preferably centrally located on the base 16, which provides stability for the housing 12. The base 16 has at least one leg 30 extending laterally outward from the base 16. The legs 30 are supported on wheels 32 or other means that will allow the apparatus 10 to be easily moved from one workstation to another. The legs 30, in a preferred embodiment, are arranged similar to a typical office chair arrangement, as shown having five legs. The legs 30 are arranged so that the apparatus 10 will have sufficient balance so that the upright member 14 may be sufficiently compact to allow accessories to be attached to the upright member 14, without interfering with the transportation of the apparatus 10. However, it should be understood that the invention would include any base leg arrangement that would allow the apparatus to be easily moved from one work area to another.

Figure 2:
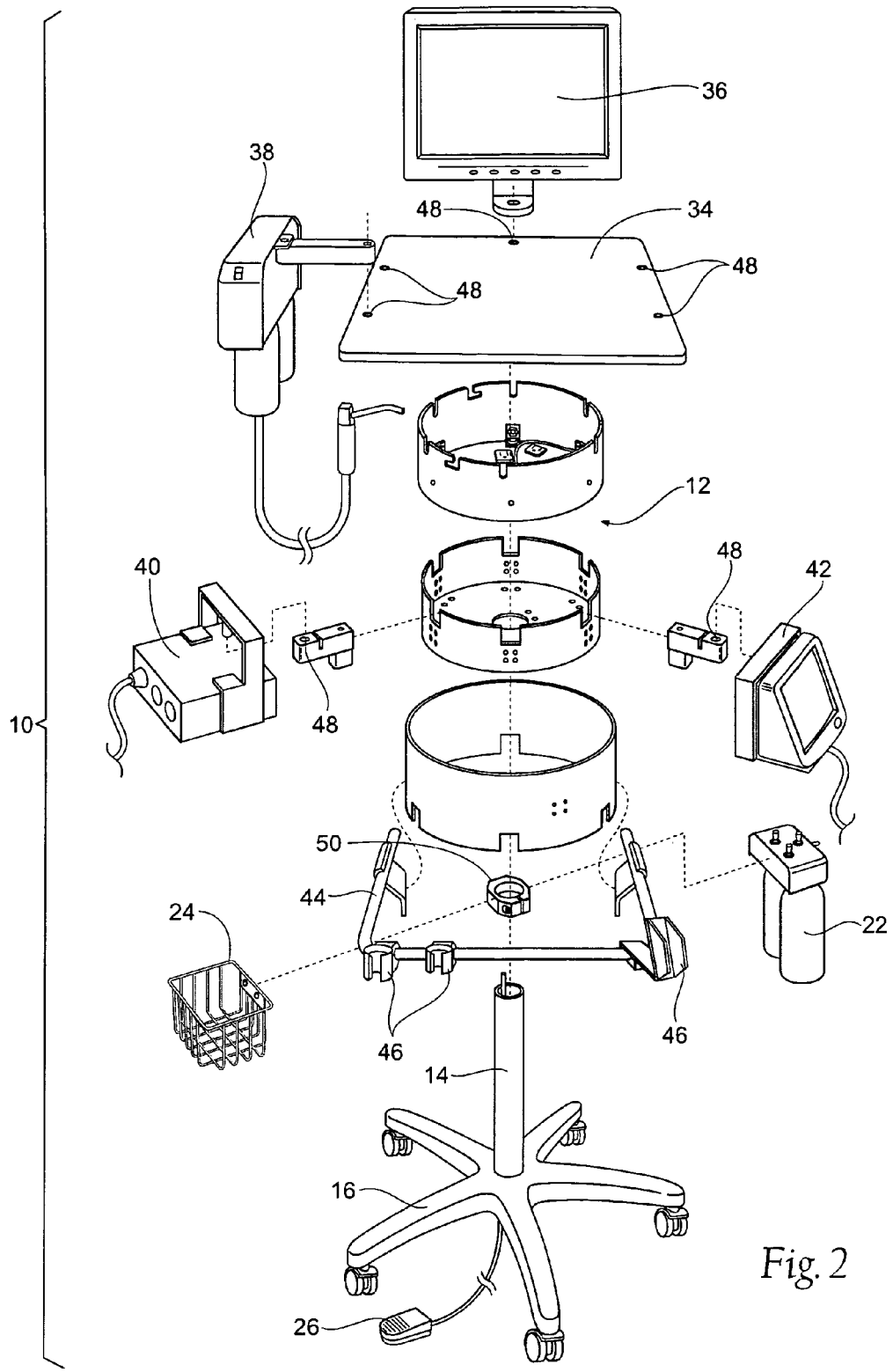
FIG. 2 is an exploded view of an equipment caddie in accordance with the present invention.

FIG. 2 provides an exploded view of the apparatus 10. The apparatus 10 is shown having more accessories attached to the apparatus 10 than in FIG. 1. For instance, a removable lid 34 that sits upon the outer shell 18 and the inner shell 20 is shown with additional accessories attached to the lid 34. A monitor screen 36 and an irrigation device 38 are shown attached to the lid 34, which preferably provides a platform above the housing 12 that can act as an operating area, if necessary. The arrangement of FIG. 2 further exemplifies the adaptability and modular features of the apparatus 10.

In addition to the accessories attached to the lid 34, several further accessories and attachments are shown arranged upon the housing 12. A control panel 40 and a diagnostic machine 42 are attached to the housing 12. The attachment means for these accessories will be discussed with more detail with respect to FIGS. 10 and 11. Similarly, a bar 44 that provides further support means 46 for a number of surgical tools (not shown) may also be attached to the housing 12. These accessories are shown as one potential arrangement of the apparatus 10 and to exhibit the adaptability of the apparatus 10 and should not be considered as limiting the scope of the invention or the possible accessories that may be utilized in connection with the present invention. For instance, a plurality of apertures 48 for attaching the accessories to the apparatus 10 is situated in various places on the apparatus 10. The apertures 48 are preferably of the same dimension, which allows the accessories to be arranged and rearranged for a person's individual needs.

Still referring to FIG. 2, a clamp 50 is situated around the upright member 14 to provide attachment means for the fluid reservoir 22 and the storage bin 24. The clamp 50 may be of any shape, but, as shown, allows for an adjustable height of the fluid reservoir 22 and the storage bin 24. The arrangement of the upright member 14 and the housing 12 allows the housing 12 to form a protective overhead cover for the fluid reservoir 22. This is an improvement over previous caddie designs in that it provides for easy access to the fluid reservoir 22 while still protecting the reservoir 22 from possible damage. A user may refill or replace the reservoir 22 without having to access the interior of the caddie or the component or accessory housing, as is necessary with the prior art. Once again it should be noted that any number of accessories may be attached to the upright member 14 and the aforementioned attachments should not be considered limiting on the invention.

Figure 3:
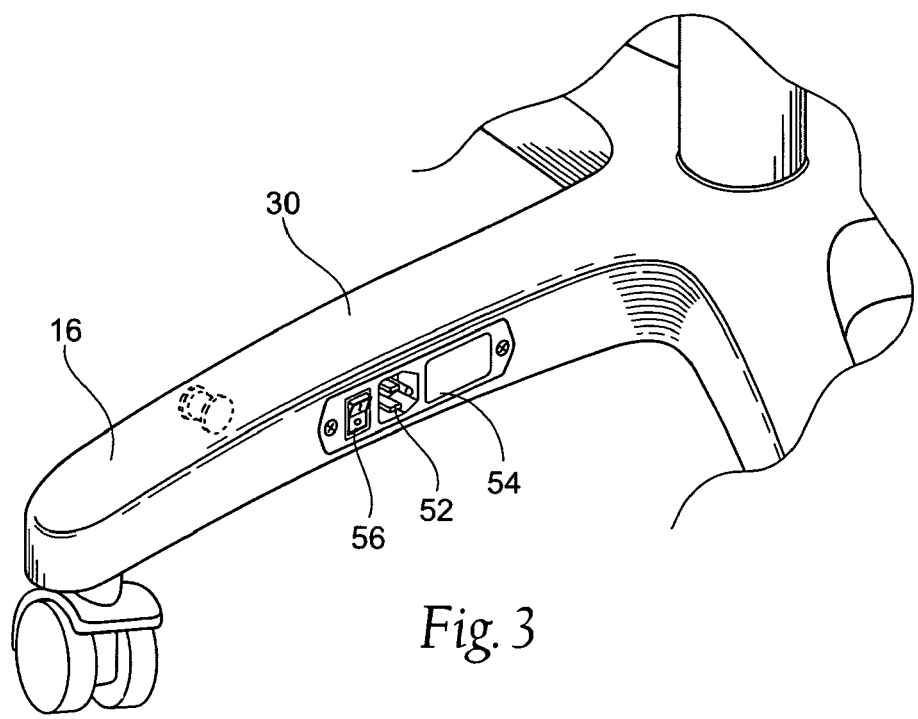
FIG. 3 is a close-up cut away view of a base section of an equipment caddie in accordance with the present invention.

FIG. 3 shows a close-up cut-away view of the base 16 and one of the laterally extending legs 30. The leg 30 may be arranged with at least one electrical aperture 52, which provides an area for attachment of a power cord (not shown) to an electrical connector 54, with the power cord connected to a power supply (not shown). A power switch 56 is provided as an auxiliary device to stop electrical flow from the power supply. The aperture 52 provides connection means to a conduit located within the leg 30 (see FIG. 5). The electrical aperture 52 provides a quick and easy place for electricity or power to be furnished to the apparatus 10 in an efficient manner that will minimize interference with the mobility of the apparatus 10. It is understood that the apparatus or equipment caddie 10 could be designed with more electrical connectors and apertures and still fall within the scope of the present invention.

Figure 4:
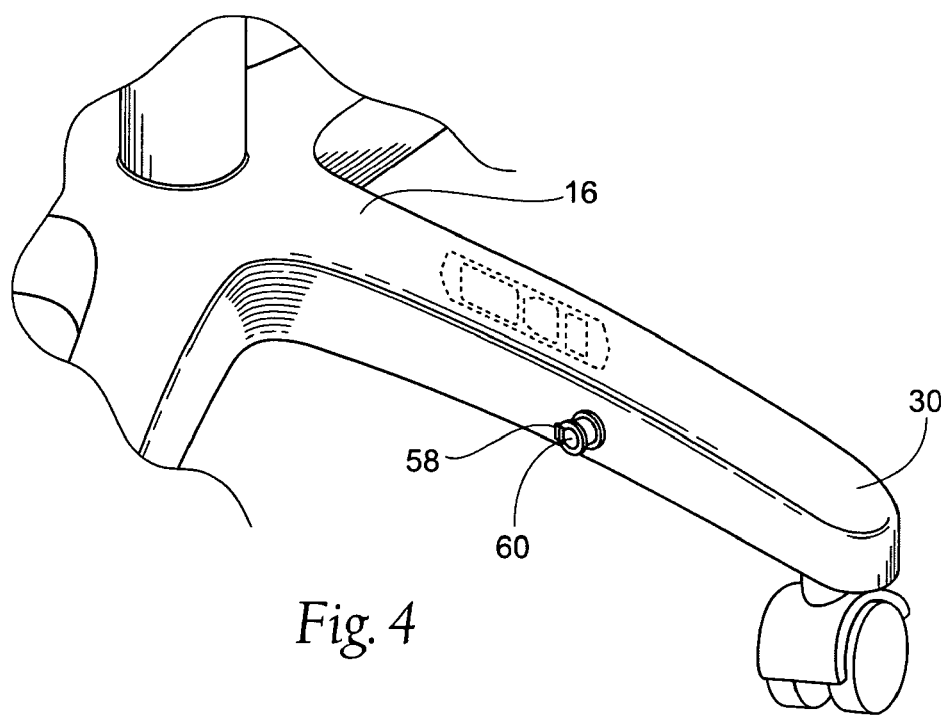
FIG. 4 is another perspective view of the base shown in FIG. 3.

FIG. 4 shows a close-up cut-away of the base 16 and one of the legs 30 taken from a different angle than that shown in FIG. 3. A fluid/air port 58 is located on the leg 30 for attachment to an external fluid source (not shown). The port 58 may have a removable cover 60 that allows closure of the port 58 when not in use. The external fluid/air source is preferably a pressurized air source. The port 58 is connected to a conduit or fluid/air line (see FIG. 5) for dispersion of the fluid/air various devices and attachments located on the apparatus 10. Preferably, as shown by the phantom arrangements of FIGS. 3 and 4, the fluid/air port 58 and the electrical aperture 52 are located on the same leg 30, thereby minimizing the area where external lines and cords are attached to the apparatus 10. However, this is not necessary, and either the aperture 52 or the port 58 may be located separately on any of the legs 30. Similarly, as noted with respect to the FIG. 3 and the power source, it is possible to have more than one fluid/air pathway and fluid/air port 58 within the equipment caddie or apparatus 10 and still fall within the scope of the present invention.

Figure 5:
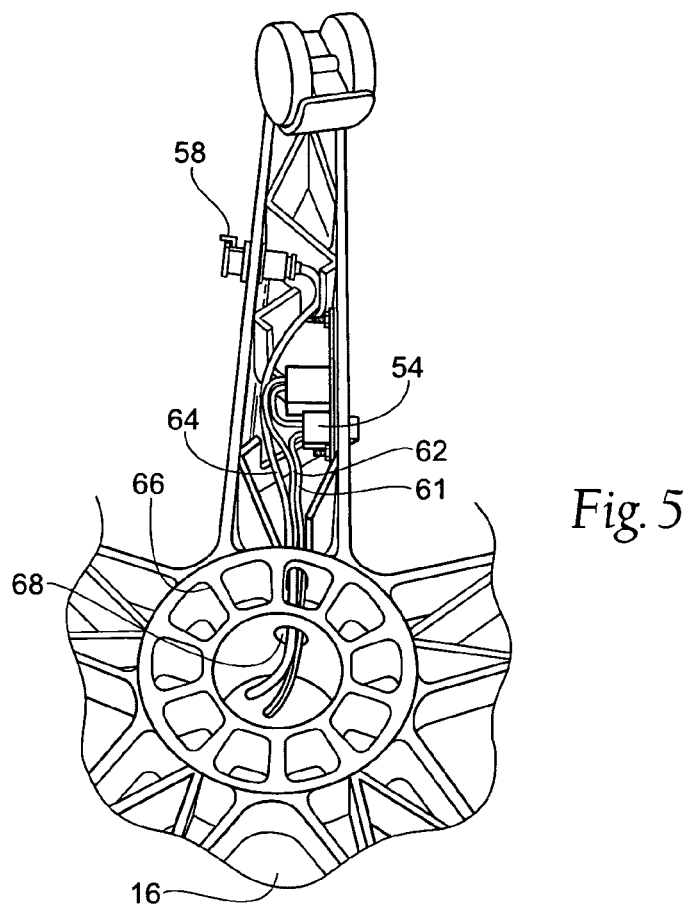
FIG. 5 is a bottom view of the base shown in FIG. 3.

FIG. 5 provides a bottom view of the leg 30 discussed with respect to FIGS. 3 and 4. The underside of the leg 30 is generally hollow, allowing for a channel or conduit 61 to pass through the leg and to house supply lines from the power and fluid/air sources. The channel 61 provides an area for an electrical conductor or power line 62 and a fluid/air line 64 to travel from the electrical connector 54 and the fluid/air port 58, respectively, towards a center section 66 of the base 16. The channel 61 is shown to contain both the conductor 62 and fluid/air line 64. However, it is understood that separate channels or conduits can be arranged for each of the supply lines, whether or not the conductor 62 and the fluid/air line 64 are located in the same of different legs. The channel 61 can be arranged for any dimensions, but preferably will be sufficient to contain the conductor 62 and the fluid/air line 64 within the channel 61 in a manner that they will be enclosed by the leg 30 when in a normal use position and will not interfere with the movement of the apparatus 10. The conductor 62 and the fluid/air line 64 are shown traveling through an opening 68 located in the center section 66. The opening 68 is not required, and it may be preferable to not pass the conductor 62 and the fluid/air line 64 through the opening 68 or a similar hole for ease of removing the conductor 62 or the fluid/air line 64, if necessary.

Figure 6:
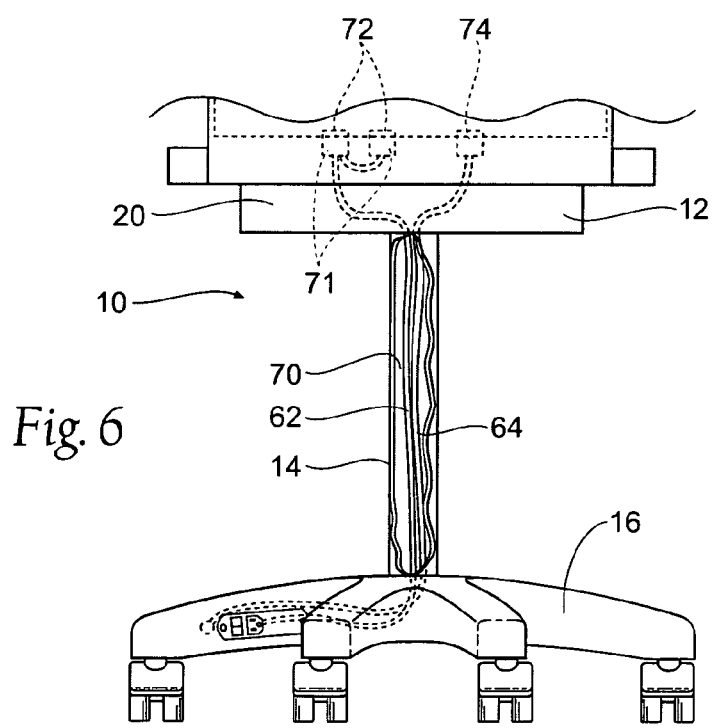
FIG. 6 is a partially cut-away side view of an equipment caddie according to the present invention.

FIG. 6 shows a partially cut-away side view of the apparatus 10. The upright member 14 has been cut-away to show a passageway 70 that allows the conductor 62 and the fluid/air line 64 to pass upward from the base 16, through the upright member 14, into the inner shell 20 of the housing 12. The conductor 62 will be connected to at least one electrical receptacle 71, which in turn connects to at least one electrical outlet 72 (shown in phantom). The fluid/air line 64 will be connected to at least one fluid/air outlet 74, respectively. Depending on the requirements for a specific apparatus, any number of electrical outlets 72 or fluid/air outlets 74 may be utilized in the present invention. The upright member 14 is shown as being tubular and centrally located with respect to the housing 12 and the base 16. Also, the upright member 14 is shown as completely encircling the passageway 70. It is to be understood that the passageway 70 may be open on one or more sides and still fall within the scope of the present invention. For example, if the upright member 14 had an open, semi-circular shape, it still could provide a passageway for a conductor or conduit to pass through.

Figure 7:
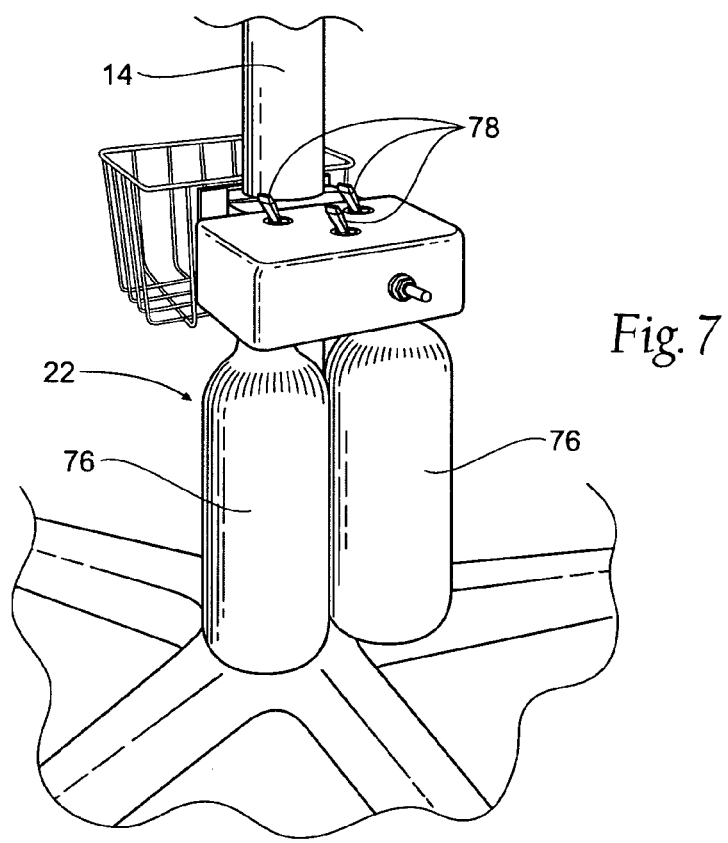
FIG. 7 is a sectional view of the equipment caddie shown in FIG. 1.

Referring to FIG. 7, another view of the upright member 14 is shown. The fluid reservoir 22 is depicted having two holding tanks 76. The holding tanks 76 may contain any desired fluid, such as antiseptic, water, or other possible medicinal fluids. Control switches 78 located on the reservoir 22 will provide the operator with control over which of the holding tanks 76 is in use or other functions of the reservoir 22. As previously stated, the overall arrangement of the apparatus 10 allows the reservoir 22 not to interfere with a person's movement or space when using the apparatus, while still providing easy access to the reservoir 22, if necessary. Likewise, because the reservoir is situated exteriorly of the equipment housing, it will be easier to attach and remove the reservoir 22, as compared to the prior art.

Figure 8A:
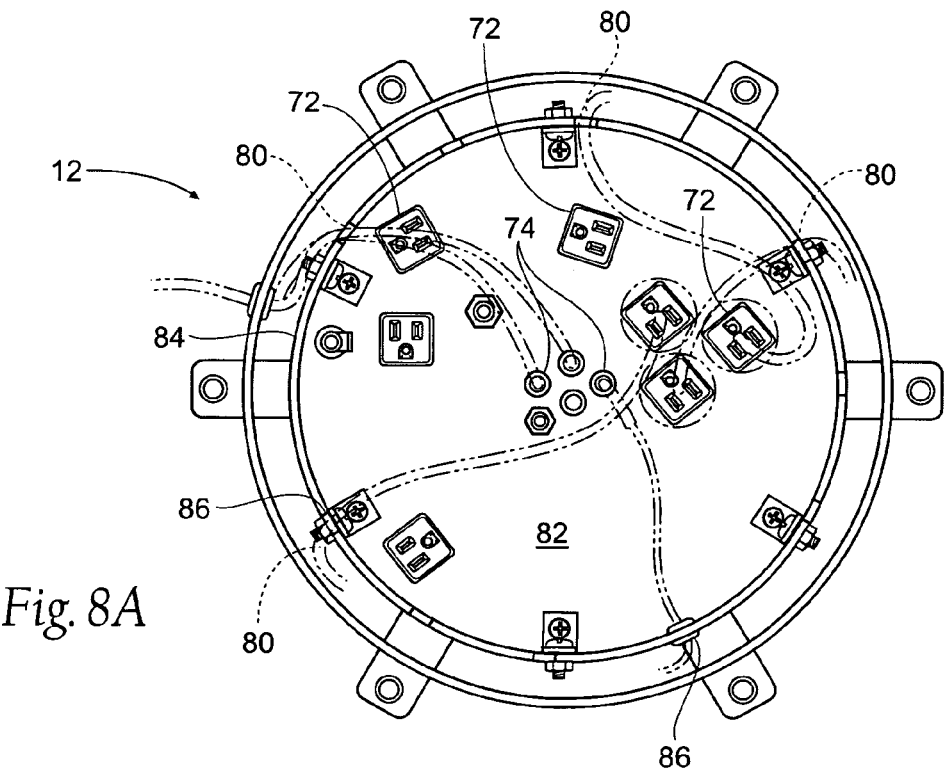
FIG. 8A is an overhead view of a housing section of the equipment caddie shown in FIG. 1.

FIG. 8A shows an overhead view of the housing 12. As previously stated, the inner shell 20 of the housing 12 is spaced apart from the outer shell 18 of the housing 12, preferably in a concentric arrangement as shown. The space between the shells 18 and 20 provides an area for any number of supply cords 80 (shown in phantom) to be passed through to any of the attached accessories or tools. The housing 12 may be designed with a single shell, but the dual shells allows for more flexibility and room for arranging the supply cords 80. The supply cords 80 should be understood to include both electrical and fluid/air supply cords. The arrangement of the outer shell 18 and the inner shell 20 provides a protective raceway for the supply cords 80 when transporting or moving the apparatus, while allowing the cords to be positioned in an open, easily manageable arrangement.

Still referring to FIG. 8A, the inner shell 20 is shown comprising a bottom section 82 with a wall 84 extending upwardly from the bottom section 82. A plurality of receiving areas 86 is located on the wall 84. The receiving areas 86 provide support for the supply cords 80. The receiving areas 86 are shown as through bores that the cords 80 will pass through. It should be understood that any arrangement that provides organization for the supply cords 80 as they extend outward from the inner shell 20 and the bottom section 82 should be included as equivalent to the shown receiving areas. For instance, notches or grooves in the wall 84, straps, loops, clamps, or other retaining devices could replace the receiving areas 86 as shown, and the arrangement would still fall within the scope of the invention.

Referring further to FIG. 8A, the plurality of electrical outlets 72 are shown located on the bottom section 82 of the inner shell 18. The outlets 72 provide easy connecting means for electrically powered surgical tools or accessories. The arrangement is an improvement over previous designs because the outlets 72 are easily accessible, which allows for easy connection of the tools or accessories to the apparatus 10, with the tools or accessories located essentially externally of the apparatus 10. Thus, for example, if a tool needs to be repaired, only the tool needs to be replaced, and the entire apparatus 10 does not need to be taken in for service. Likewise, the apparatus 10 may be designed with more outlets 72 than tools or accessories actually used. If a specific outlet 72 was not properly functioning, the tool may be moved to another outlet 72, which further minimizes downtime and increases utility of the apparatus 10.

The fluid/air outlets 74 are also shown in the bottom section 82 of the inner shell 20. As with the electrical outlets 72, the fluid/air outlets 74 provide efficient means for accessing and removing one of the connected tools or accessories, if necessary. It should be understood that the bottom section 82 should be considered the area that houses the outlets 72 and 74 and should not be limited to any specific spatial arrangement. For instance, it could be possible that the bottom section 82 is integral or unitary with the upstanding wall 84. Such an arrangement would still fall within the scope of the present invention.

Figure 8B:
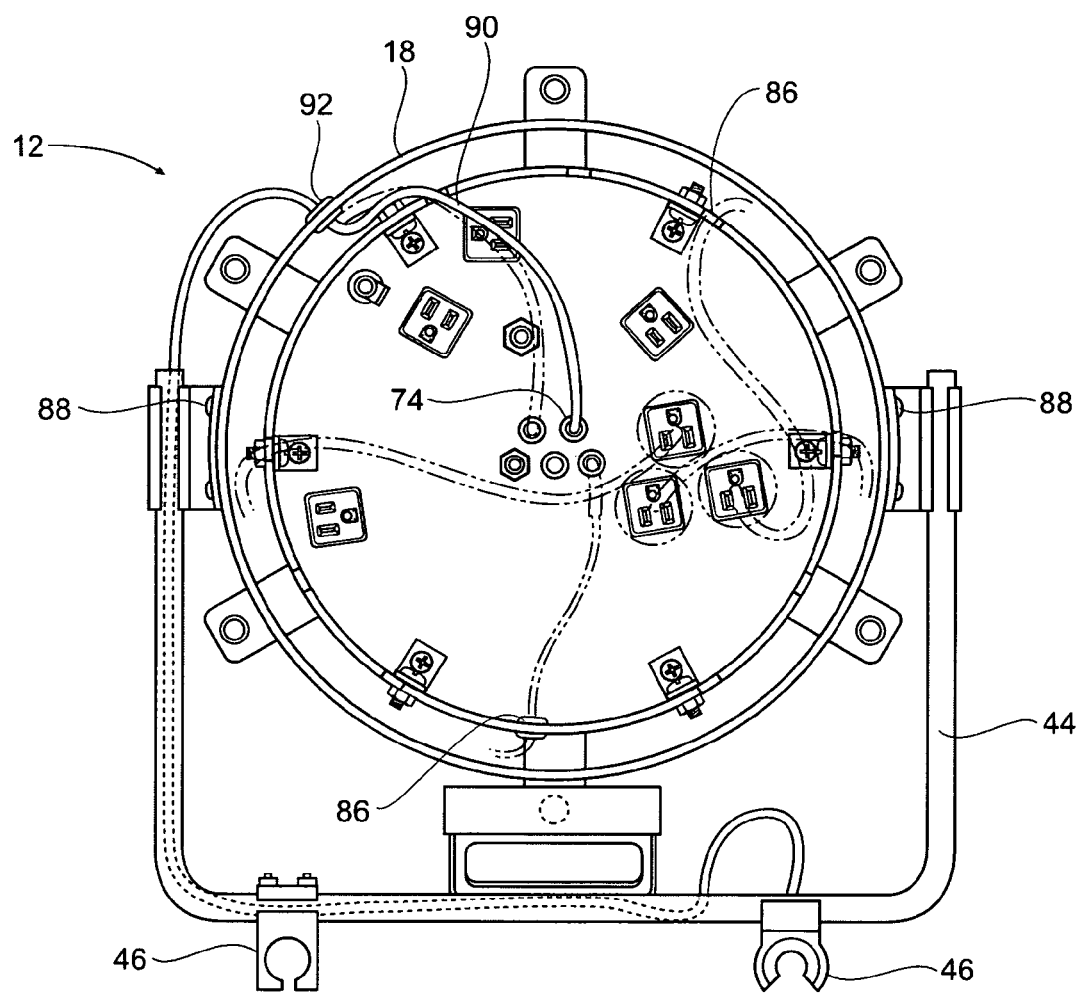
FIG. 8B is an overhead view the housing section of FIG. 8A further containing a tool support device.

FIG. 8B is an overhead view of the housing 12, further including the bar 44. The bar 44 is attached to opposing sides of the outer shell 18 by a pair of brackets 88. The bar 44 holds various support means 46 for various tools, as previously discussed. The support means 46 may be adapted to hold and secure any specifically designed surgical tool or accessory. The bar 44 may be hollow, which would allow one of the supply lines 80 to pass through the bar to one of the attached tools or accessories. For instance, a fluid/air supply line 90 is shown connected to one of the fluid outlets 74. The fluid/air supply line 90 passes through the receiving area 86 and through an outer receiving area 92 located in the outer shell 18 of the housing 12. The supply line 90 enters the bar 44 and will exit at or near any appropriate support means 46. When moving or orienting the apparatus 10, the bar 44 also provides an easy area for a person to grasp the apparatus 10.

Figure 9:
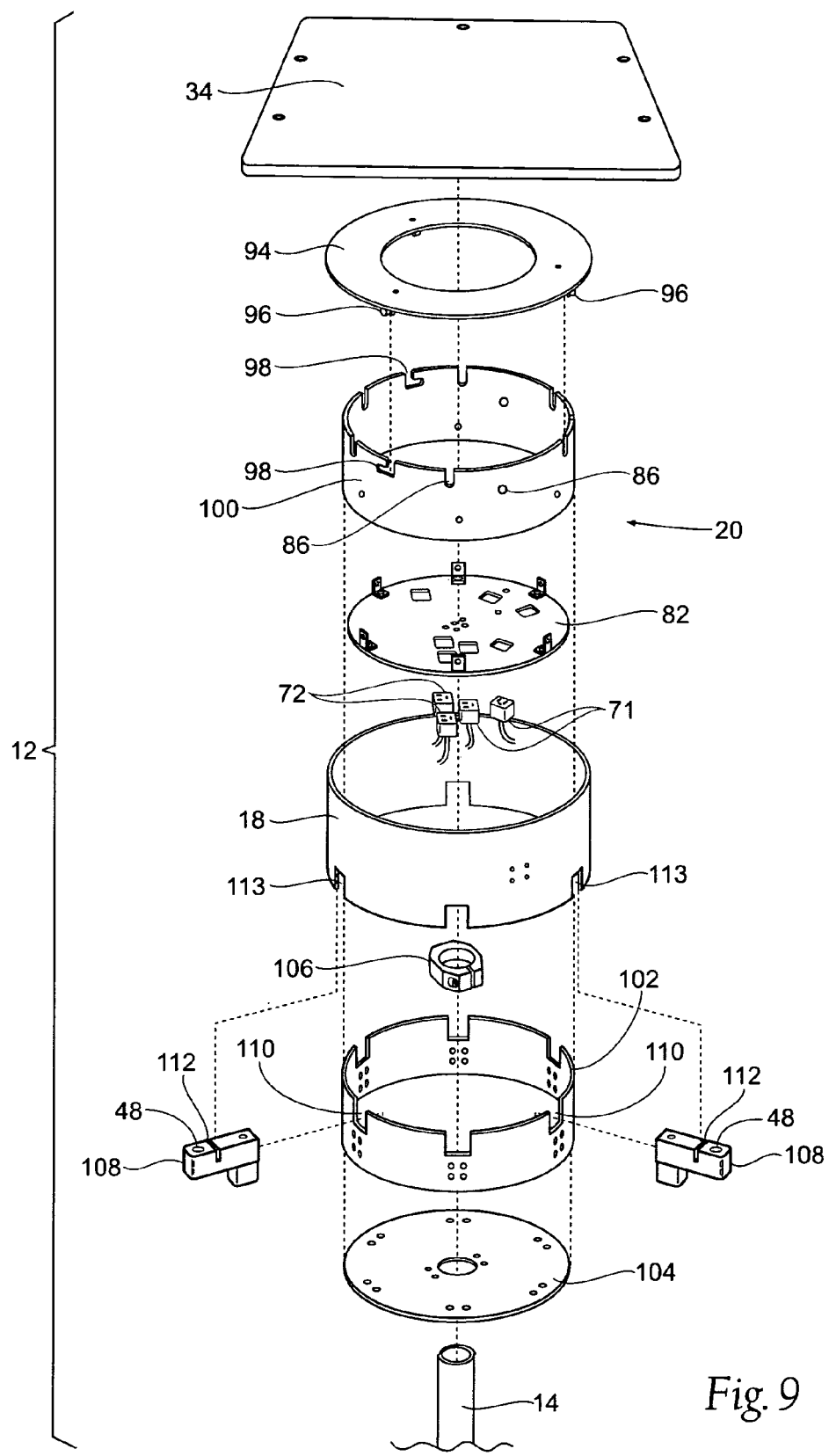
FIG. 9 is an exploded view of a housing section in accordance with the present invention.

FIG. 9 shows an exploded view of the housing 12 and the lid 34. The lid 34, as previously stated, can have a planar surface that will act as a workstation for the attending medical personnel. A securing section 94 is located on the underside of the lid 34. Protrusions 96 located on the underside of the lid 34 will mate with L-shaped notches 98 located on the inner shell 20. The notches 98 and the protrusions 96 mate in such a way that the lid 34 may be easily placed upon the housing and turned to lock the lid 34 and the housing 12 together, thereby providing a protective cover for the outlets and cords located within the housing 12. The arrangement also allows for the lid 34 to be easily removed from the housing 12 by turning the lid in the opposite direction from that which locked the lid 34 in place, without interfering with the receiving areas 84 when secured to the housing 12. The securing section 94 may also be arranged so that the lid 34 is secured to the outer shell 18 and not the inner shell 20. Furthermore, the lid 34 may be secured to the housing in various other forms, such as clamps, screws, or pins and should not be limited to the shown arrangement.

Still referring to FIG. 9, the inner shell 20 comprises an upper section 100 and a lower section 102. The bottom section 82 is connected to the upper section 100 by brackets or any other conventional means. The underside of the bottom section 82 is connected to the lower section 102, which is, in turn, connected to a second bottom section 104. All of the components may be connected in any suitable connecting means. A securing clamp 106 is used to hold the second bottom section 104 to the upright support member 14. The two-tiered arrangement of the inner shell 20 provides protection for the outlets 72 and 74 (see FIG. 8A) in the upper section 100 and separately provides protection for the electrical receptacles 71 within the lower section 102. While it is possible to arrange the housing 12 so that the electrical receptacles 71 are not enclosed within the lower section 102 of the inner shell 104, the design as shown provides additional protection for the receptacles 73. The overall arrangement provides for an efficiently organized, protective housing 15.

Referring further to FIG. 9, the inner shell 20 will sit within the outer shell 18. Bracket supports 108 rest within openings 110 located within the lower section 102. The brackets supports 108 are secured to the second bottom section 102 and extend outwardly of the inner shell 20. Slots 112 located on the bracket supports 108 provide a mating area for cavities 113 located on the outer shell 18. Located further outward of the slot 112 on the bracket support 108 is one of the apertures 48, discussed with respect to FIG. 2, for holding tools or accessories. The brackets 108 provide a straightforward way to align the inner shell 20 and the outer shell 18 so that they are secured together in an efficient manner that is easily assembled.

Figure 10:
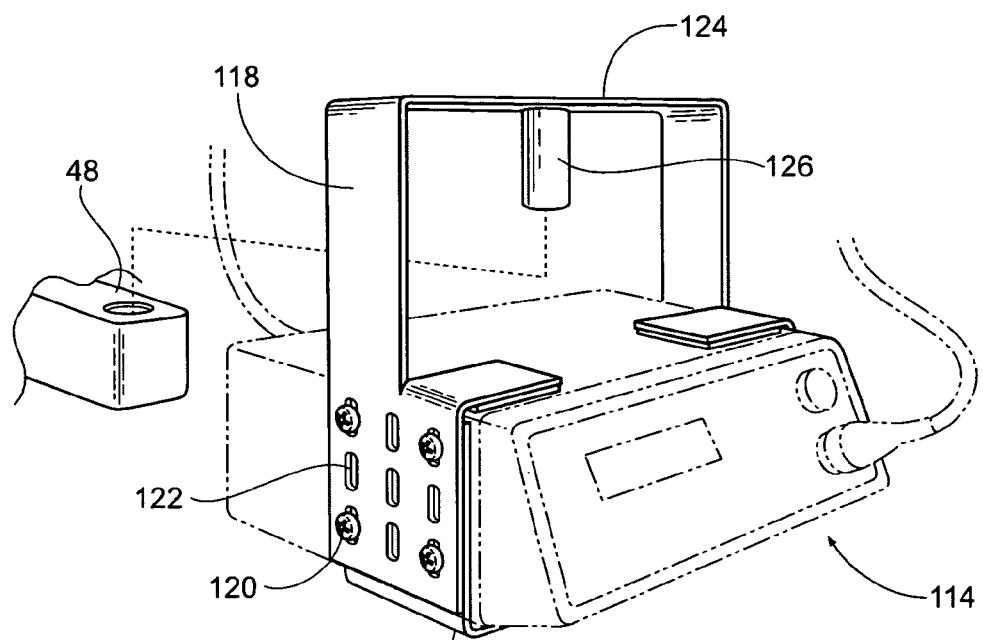
FIGS. 10-13 show perspective views of possible accessory attachment devices in accordance with the present invention.

FIGS. 10 through 13 show possible attachment devices for attaching accessories to the equipment caddie. The structures are universal devices that may be attached to a wide range of medical devices, monitors, controllers, and similar devices from various companies. FIG. 10 shows an overhead attachment device 114. The device 114 comprises a base section 116 for supporting a medical device (shown in phantom). The base section 116 is joined to an upright section 118. The base section 116 and the upright section 118 are joined together with screws, bolts, or other attachment means 120 in a slotted area 122. Alternatively, the base section 116 and the upright section 118 could be an integral piece. The upright section 118 comprises a crossbar 124 that has a shaft 126 extending downwardly from the crossbar 124. The shaft 126 matingly and removably fits within the aperture 48. The shaft 126 is preferably perpendicular to the crossbar 124.

Figure 11:
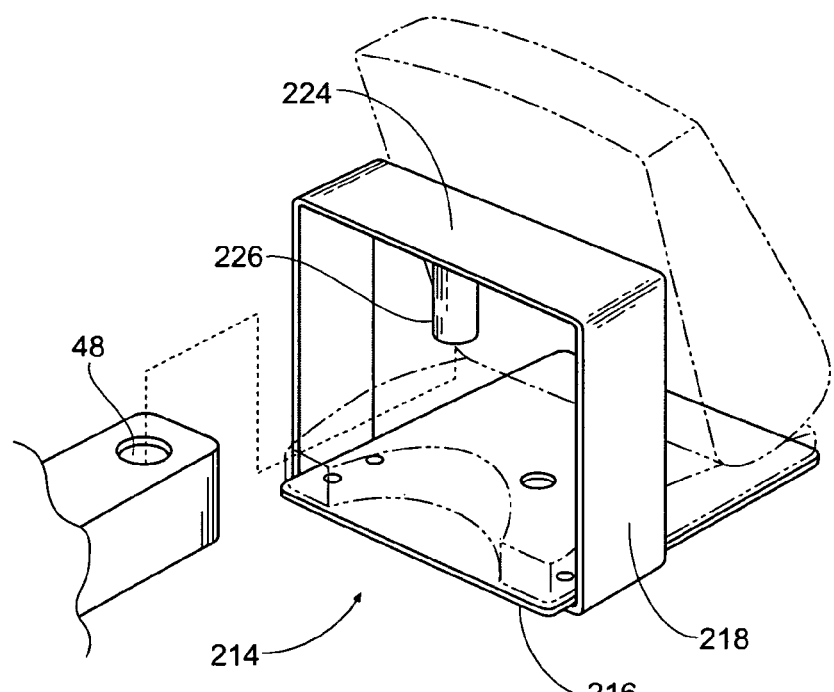

FIG. 11 shows another attachment device 214. The device 214 allows for an accessory (shown in phantom) to be attached to the equipment caddie (not shown) at the rear of the accessory. The device 214 has a base section 216 and an upright section 218 that are integrally formed. Similar to the device 114, the upright section 218 has a crossbar 224 having a shaft 226 extending downwardly from the crossbar 224.

Figure 12:
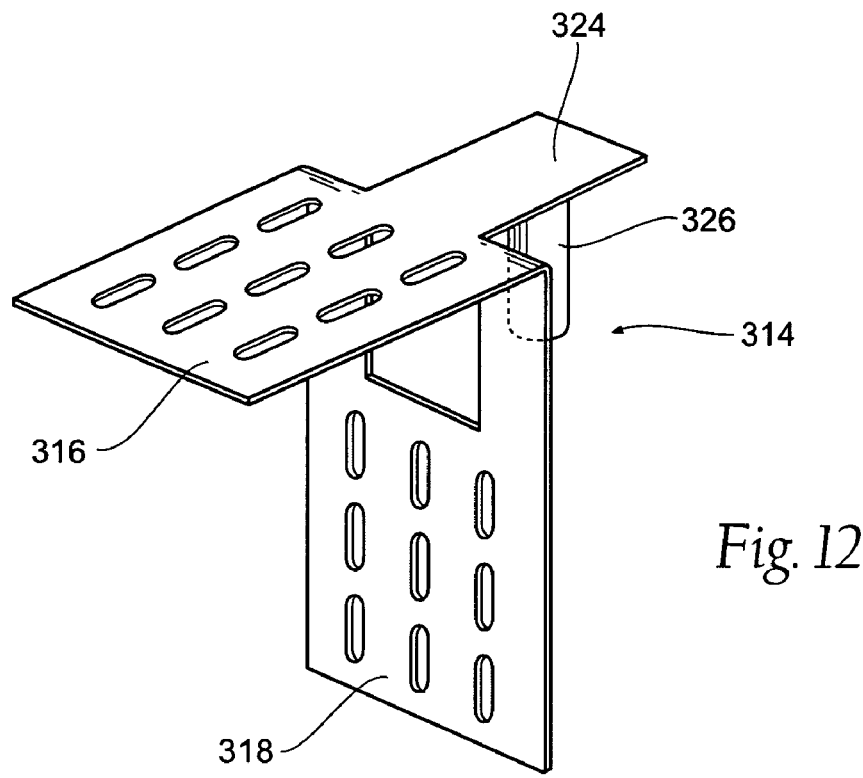

FIG. 12 shows another embodiment 314 of the attachment device. The device 314 allows for two accessories (not shown) to be attached to the same device 314. A base section 316 and an upright section 318 both would act as individual supports for separate accessories. The sections 316 and 318 would be mated with an upright section and a base section, respectively, similar to the embodiment 114 shown in FIG. 10. A crossbar 324 having a shaft 326 is arranged similar to the previous embodiments 114 and 214. That is, the shaft 326 extends downwardly from the crossbar 324 in a perpendicular arrangement, and the shaft 326 is sized to matingly fit within one of the apertures 48.

Figure 13:
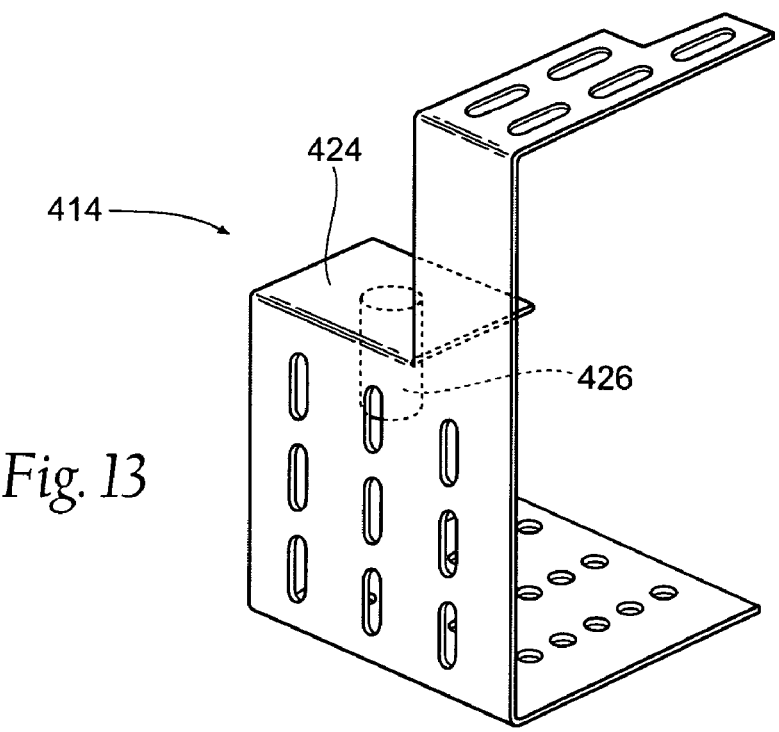

FIG. 13 shows an embodiment 414 of the attachment device similar to the device 314 of FIG. 12. The device 414 also provides a dual device attachment. A crossbar 424 has an attached shaft 426, similar to the other embodiments. Provided that the universal device has a support area for an accessory and the proper shaft to removably mate with apertures 48, the device would fall within the scope of the present invention. The device allows an operator to accommodate accessories from a wide range of suppliers on a single equipment caddie. Because the arrangement of the crossbar and the shaft is consistent in all of the embodiments, the attachment devices may accommodate a wide range of different devices and manufactures simply and efficiently.

Figure 14:
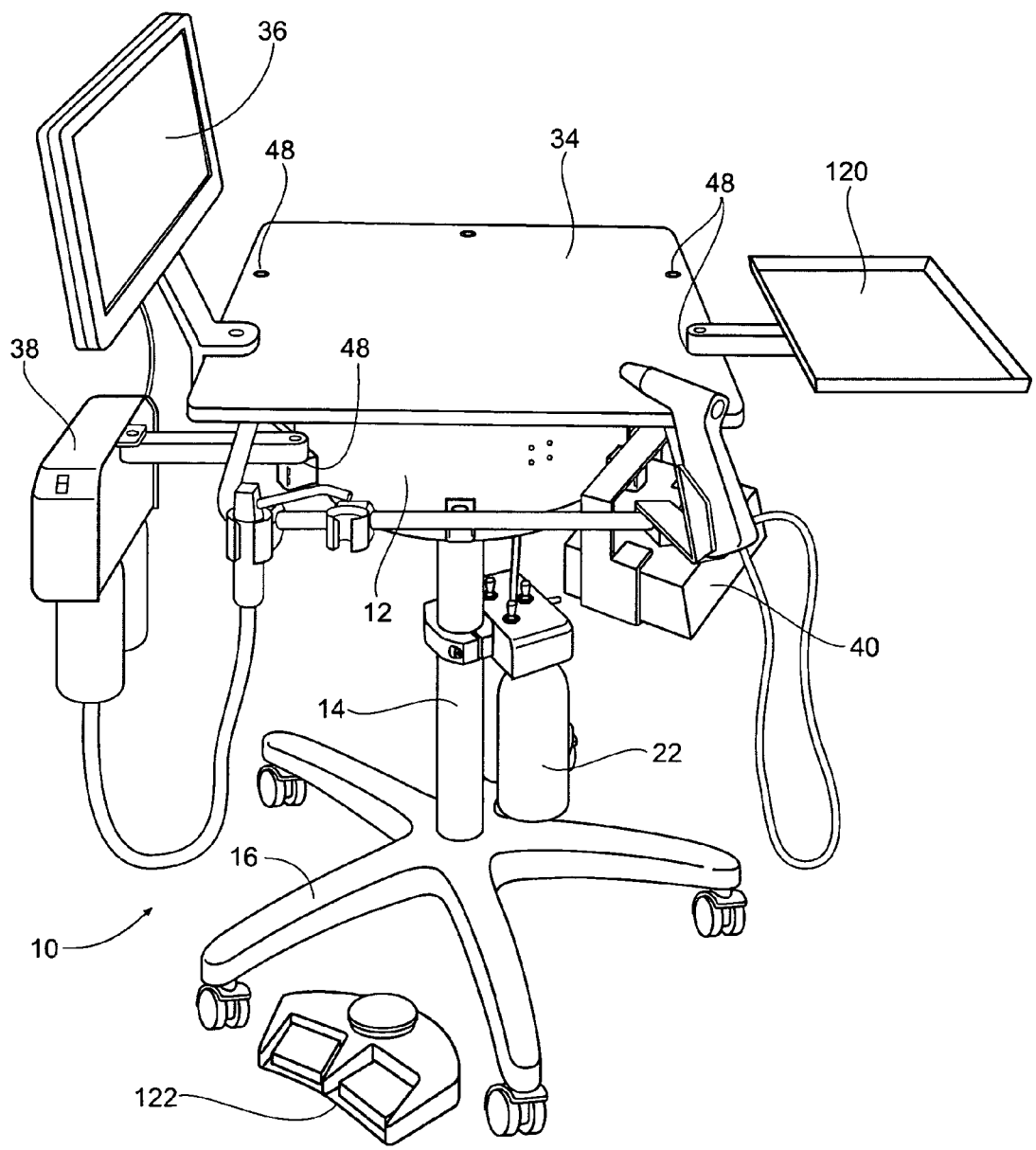
FIG. 14 is a further embodiment of an equipment caddie in accordance with the present invention.

FIG. 14 demonstrates the adaptability of the apparatus 10. Comparing FIG. 2 and FIG. 12, the monitor screen 36 is shown orientated in a different position in the two figures. Likewise, the irrigation device 38 is mounted on the housing 12 in FIG. 14, whereas it was previously mounted on the lid 34 in FIG. 2. The control panel 40 is mounted on opposite sides in the two figures. An extra tray 120 is mounted on the lid 34. Also, a wireless foot pedal 122 has replaced the foot pedal 26. Both the wireless foot pedal 122 and the foot pedal 26 may be designed to control various tools or accessories with the same pedal. For instance, switches or controls may be built into the apparatus or the pedals to allow power control to be directed towards a specific accessory. This adds to the space management features of the apparatus 10 in that fewer overall controls are needed to properly operate the tools connected to the apparatus 10.

As the figures demonstrate, the combinations are numerous, which allows for the apparatus 10 to be adapted for an individual's needs and preferences. For instance, the apparatus 10 may be easily reconfigured for use by a left-handed or right-handed person without having to move or roll the apparatus over supply cords, or needing to untangle or unwind supply cords. The apparatus 10 may be easily moved with little effort for operating on opposite sides of a patient, such as accessing teeth located on different sides of a patient's mouth.

The adaptability of the apparatus 10 is also evident in the arrangement of the components. The lid 34 may be easily lifted for access at the outlets 72 and 74 (see FIGS. 8A and 8B), which means the attached tools can be removed and stored when the apparatus 10 is not in use, if desired.

Figure 15:
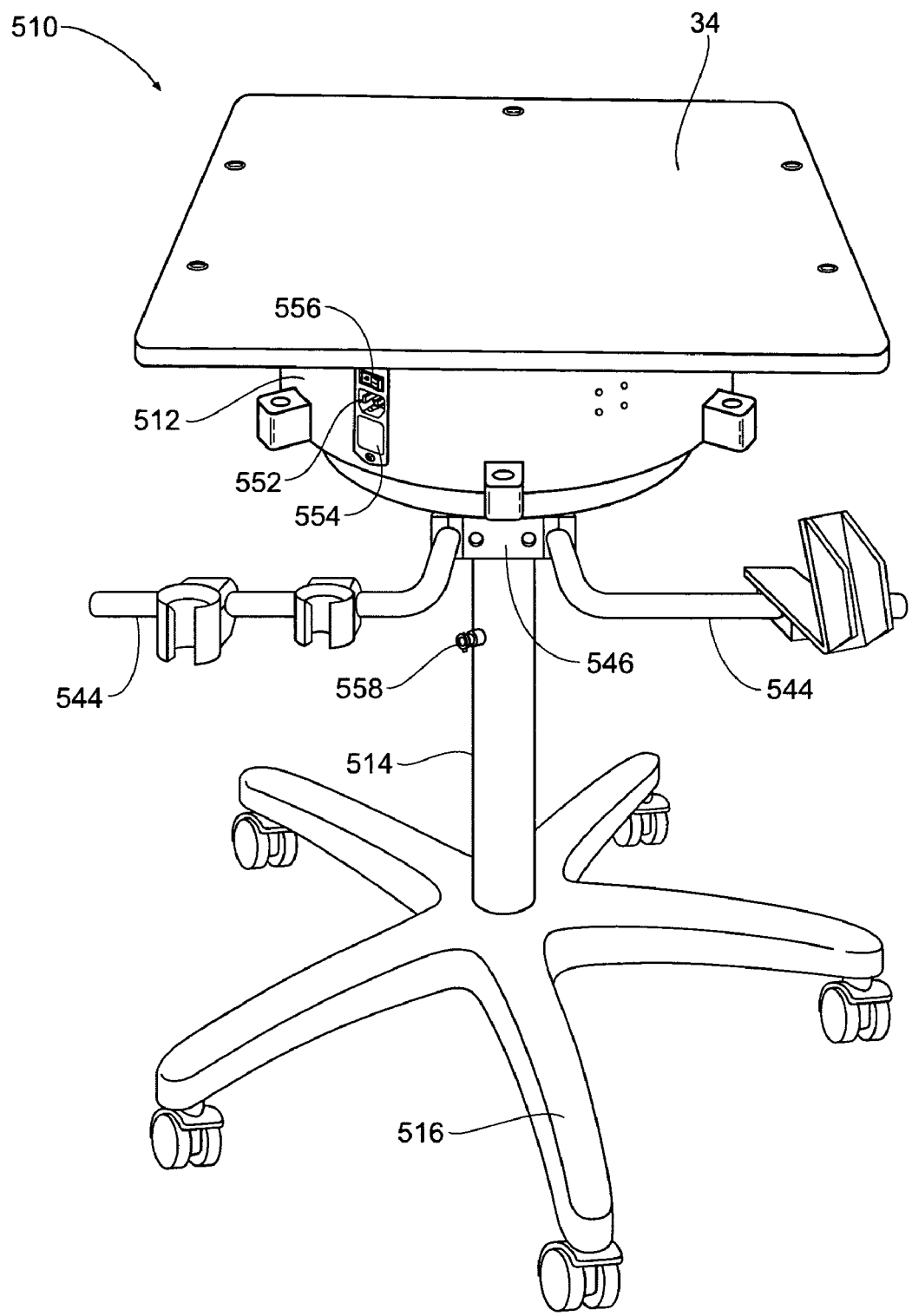
FIG. 15 is another further embodiment of an equipment caddie in accordance with the present invention.

FIG. 15 shows another potential embodiment 510 of the present invention. The apparatus 510 has a housing 512, an upright member 514, and a base 516 arranged similar to the previous embodiments. An electrical aperture 552 is located on an electrical connector 554, which allows connection of the apparatus 510 to a power supply cord connected to a power supply (not shown). The electrical connector also comprises a power switch 556 to provide an auxiliary device to stop electrical flow from the power supply. The electrical connector 554 is the same as the electrical connector 54 (see FIG. 3), except that the electrical connector 554 is located on the housing 512 instead of the base 516. There will still be an electrical conductor (not shown) that will connect the electrical connector 554 to an electrical outlet 72 (as shown in FIGS. 6 and 8A), but it is not necessary that the electrical connector travels the length of the upright member 514 and the base 516.

Still referring to FIG. 15, a fluid/air port 558 is located on the upright member 514. The fluid/air port 558 allows flow of fluid/air from an external source (not shown) to various devices, as in the prior embodiments. However, the fluid/air port 558 is not located on the base 516 and the fluid/air pathway (not shown) between the port 558 and the fluid/air outlets (see FIG. 8B) would be shorter than the prior embodiments. As is evident by FIG. 15, the electrical aperture 552 and the fluid/air port 558 may be located on any area of the apparatus 510 and still fall within the scope of the present invention. It should be understood that both the electrical conductor and the fluid/air pathway are not limited to any specific place within the apparatus. Provided that each forms a path for fluid/air and electricity to flow to the respective outlet from the part or aperture, the arrangement would fall within the scope of the present invention.

FIG. 15 also provides an alternate handle bar arrangement. The handle bar arrangement comprises two individual, oppositely disposed handlebars 544. The handlebars 544 are fastened to the upright member 514 by fastening means 546, preferably a clamp. The handlebars 544 may be adjusted to any preferred height and may be angled upwardly or downwardly if desired by adjusting the clamp 546. As the apparatus 510 shows, the present invention in numerous designs, which further enhances the mobility and universality of the invention.

Figure 16:
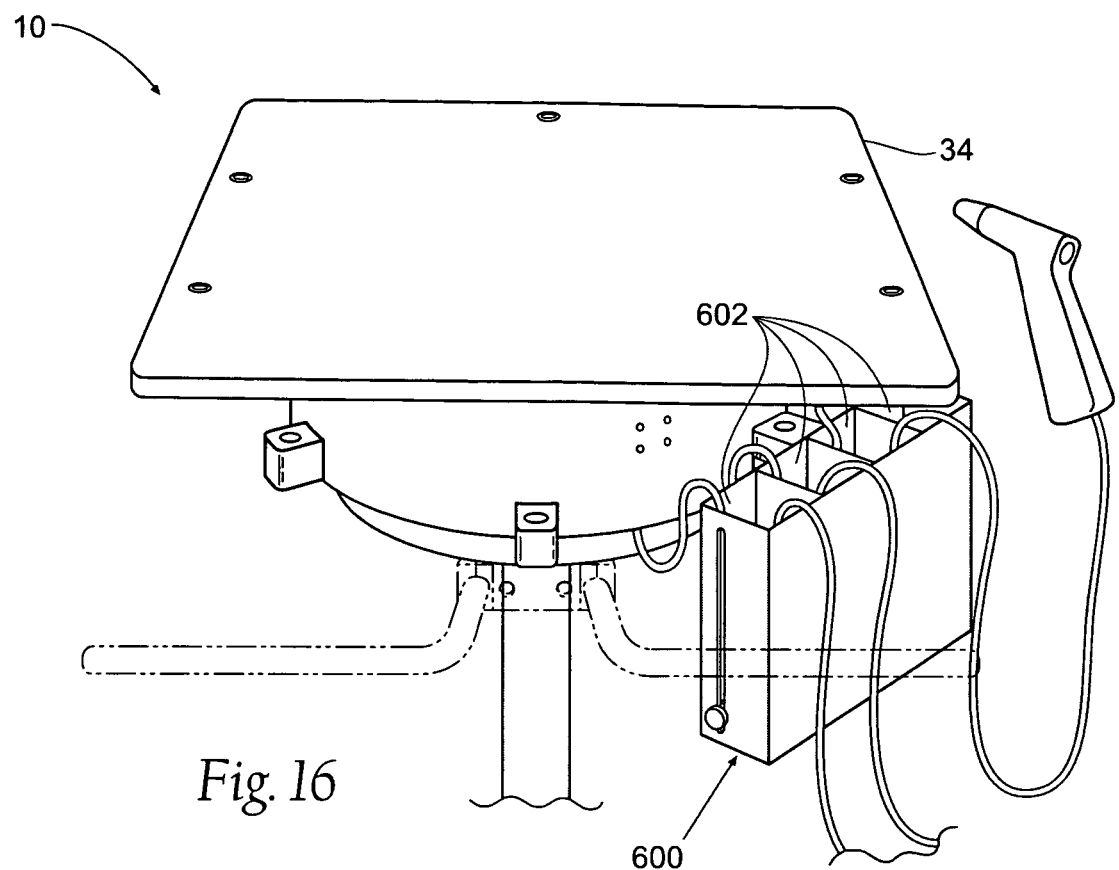
FIG. 16 is a perspective view of an attachment used in connection with present invention.
Figure 17:
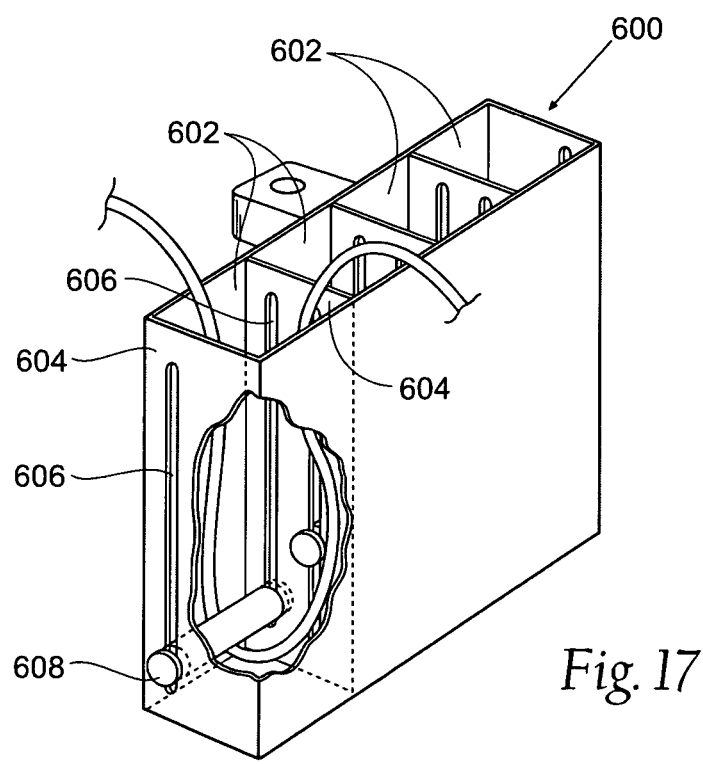
FIG. 17 is a close-up, partially cut-away view of the attachment shown in FIG. 16.

FIGS. 16 and 17 show a further potential accessory arrangement for an equipment caddie according to the present invention. A cable management system 600 is shown. The cable management system 600 allows the cords and cable of the various dental attachments to be organized on the equipment caddies. Each cord or cable is passed through an individual silo 602. The silo 602 has a pair of oppositely disposed sidewalls 604, each preferably containing a guide slot 606. A guide pin 608 is retained within the guide slots 606. When a dental attachment is to be used, the operator takes the dental attachment and positions it as necessary. The cord will be extended, thereby pulling upwards on the guide pin 608. When the dental attachment is returned to a stored position, the guide pin 608 will move downwardly, which will assist in storing the cord without getting the cord tangled with other cords. The guide pin 608 may be weighted or comprise a spring or other device that will move the guide pin 608 into the stored position. Likewise, the management system 600 could take other forms as currently shown and still fall within the scope of the present invention. For instance, the guide means could be designed differently than the guide pins and guide rails currently shown.

Figure 18:
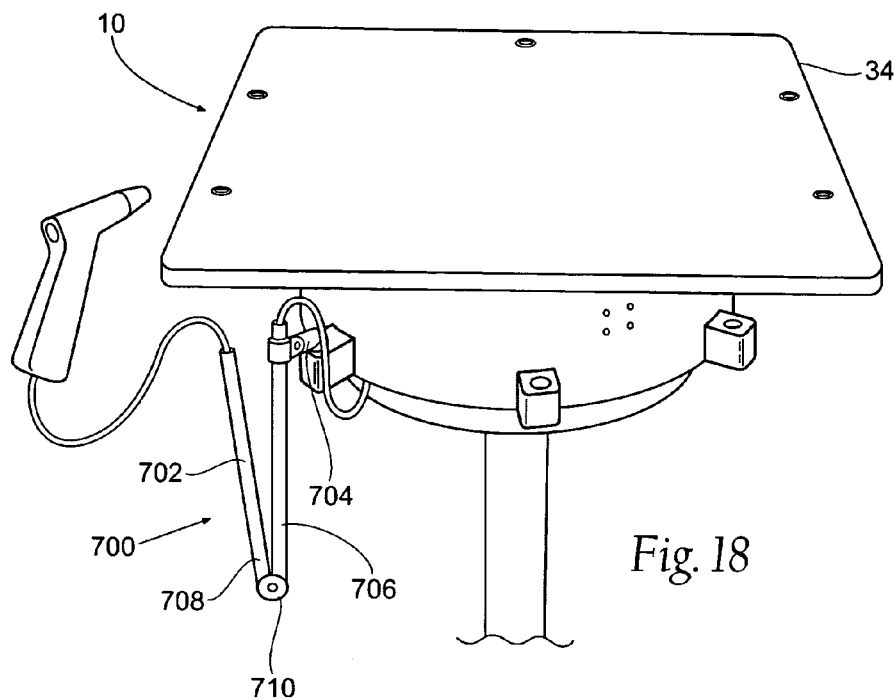
FIG. 18 is a perspective view of an attachment used in connection with present invention.
Figure 19:
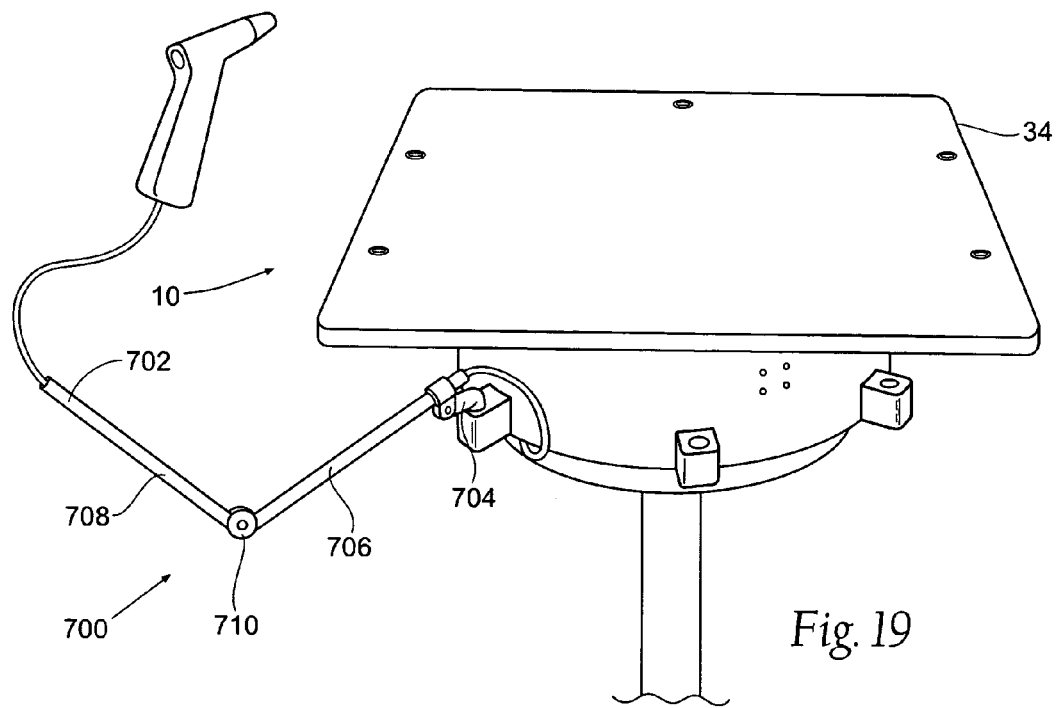
FIG. 19 is a perspective view of the attachment shown in FIG. 18 in a second position.

FIGS. 18 and 19 show an alternate cable management system 700 from the system shown in FIGS. 16 and 17. The cable management system 700 generally comprises a sheath 702 that is open on both ends to allow the cord or cable of the various dental attachments to pass through the sheath 702. The sheath 702 is preferably made of a lightweight, sturdy material. The sheath 702 may be attached to the apparatus 10 by a support or brace or other attachment means 704 that will not interfere with movement of any of the various cords or cables. The attachment means as shown could be a shaft and aperture, as described previously for attachment of other devices (see, e.g., FIG. 11). Alternatively, the sheath 702 could be designed so it is not necessary for the sheath 702 to be attached to the apparatus 10. As shown, the sheath 702 consists of a first section 706 and a second section 708 connected together by a hinge joint 710. The hinge joint 710 allows the sheath 702 to be contracted or extended as necessary and also allows the specific dental instrument to be stored easily along the side of the apparatus 10. Several sheaths 702 could be used in conjunction to manage several dental instruments.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A portable medical apparatus for holding a plurality of surgical tools wherein at least one of said tools is electrically powered and includes a power supply cord and a power plug, said apparatus holding at least one surgical accessory including a fluid supply cord, said apparatus comprising:

a housing, said housing comprising;

an upper section having a first bottom section and an upstanding wall, said upper section allowing access to at least one electrical outlet for removably receiving said power plug, said outlet being disposed within said first bottom section;

a lower section, said lower section enclosing an electrical receptacle for said at least one electrical outlet;

an upright member in supporting relationship with said housing, said upright member providing a passageway for a conductor in electrical communication with said electrical receptacle;

a base for supporting said upright member, said base including a laterally extending leg, said leg including a channel for receiving said conductor, said leg having an aperture to receive a connector for attachment to said conductor; and attachment means for said surgical tools.

2. The portable medical apparatus according to claim 1, further comprising:

a conduit for a fluid line connected to a fluid port located in said laterally extending leg in said base, said conduit extending from said base to said lower section of said housing; and at least one fluid outlet for removably receiving said fluid supply cord, said outlet located in said upper section of said housing, said fluid outlet connected to said conduit.

3. The portable medical apparatus according to claim 2, wherein said fluid line conduit is substantially coextensive with said passageway in said upright member and said channel in said laterally extending base.

4. The portable medical apparatus according to claim 1, wherein said attachment means comprises a device for removably securing said tools to said apparatus.

5. The portable medical apparatus according to claim 4, further comprising an outwardly extending bar located on said housing, said bar supporting said attachment means.

6. The portable medical apparatus according to claim 5 further comprising a pair of outwardly extending bars located on said housing.

7. The portable medical apparatus according to claim 6, wherein said lid further contains at least one aperture for receiving an accessory.

8. The portable medical apparatus according to claim 1 further including a removable enclosure lid being received by said housing.

9. The portable medical apparatus according to claim 1 wherein said housing further comprises an outer shell, said outer shell spatially arranged around said upper and said lower sections.

10. The portable medical apparatus according to claim 1 wherein said upstanding wall includes at least one area for receiving and supporting said power supply cord.

11. The portable medical apparatus according to claim 1, wherein said upright member is centrally located of said housing and said base.

12. A portable medical apparatus for holding a plurality of surgical tools wherein at least one of said tools is electrically powered and includes a power supply cord and a power plug, said apparatus holding at least one surgical accessory including a fluid supply cord said apparatus comprising:

a housing, said housing comprising;

an outer shell;

an inner shell in spatial relationship with said outer shell;

at least one electrical outlet for removably receiving said power plug, said outlet being disposed within said inner shell;

at least one fluid outlet for removably receiving said fluid supply cord, said outlet being disposed within said inner shell;

said inner shell including an upstanding wall;

an upright member in supporting relationship with said housing, said upright member providing a passageway for a conductor in electrical communication with said outlet, said upright member further providing a passageway for a conduit in fluid communication with said outlet;

a base for supporting said upright member, said base including a plurality of laterally extending legs, one of said legs including a channel for receiving said conductor, said one of said legs being apertured to receive a connector for attachment to said conductor, one of said legs including a channel for receiving said conduit, said channel receiving leg having an aperture to receive a port for attachment to said conduit; and attachment means for said surgical tools.

\* \* \* \* \*